United States Patent

Szántay et al.

[11] 4,345,082
[45] Aug. 17, 1982

[54] PROCESS FOR THE PREPARATION OF HYDROXYAMINO-EBURNANE DERIVATIVES AND OCTAHYDROINDOLOQUINOLIZINE INTERMEDIATES

[75] Inventors: Csaba Szántay; Lajos Szabó; György Kalaus; Janos Sapi; Lajos Dancsi; Tibor Keve; Maria Gazdac, all of Budapest, Hungary

[73] Assignee: Richter Gedeon Vegyeszeti Gyar Rt., Budapest, Hungary

[21] Appl. No.: 154,329

[22] Filed: May 29, 1980

[30] Foreign Application Priority Data

May 31, 1979 [HU] Hungary ................ RI 713

[51] Int. Cl.³ ............... C07D 461/00; C07D 455/00; A61K 31/475
[52] U.S. Cl. ........................ 546/51; 546/70; 424/256
[58] Field of Search ............ 546/51, 70; 424/256

[56] References Cited

U.S. PATENT DOCUMENTS 3,755,333  8/1973  Szántay et al. ............ 546/51
4,035,370  7/1977  Lörincz et al. ............ 546/51
4,173,642  11/1979  Szántay et al. ............ 546/70 X
4,190,658  2/1980  Warnant et al. ............ 424/256

FOREIGN PATENT DOCUMENTS 53-147100  12/1978  Japan ............ 546/51

Primary Examiner—Donald G. Daus
Assistant Examiner—Diana G. Rivers
Attorney, Agent, or Firm—Karl F. Ross

[57] ABSTRACT

The invention relates to new hydroxyamino-eburnane derivatives of the general formula (I),

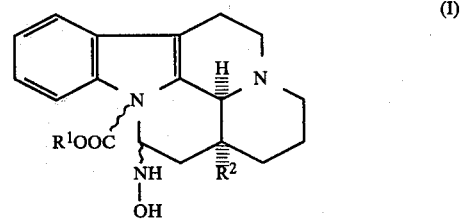

wherein $R^1$ and $R^2$ each stand for a $C_{1-6}$ alkyl group, as well as to pharmaceutically acceptable acid addition salts and optically active isomers of these compounds.

These new compounds can be applied as peripheral vasodilatating agents or can be converted into other compounds, e.g. vincamine and apovincamine derivatives of valuable therapeutic effects.

The compounds of the general formula (I) are prepared according to the invention by reacting a hexahydro-indoloquinolisinium derivative of the general formula (II),

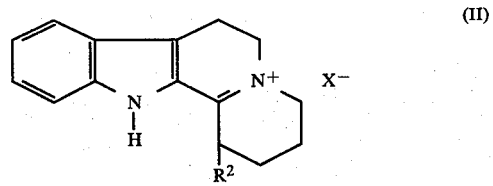

wherein $R^2$ is as defined above and X stands for an acid residue, with a methylenemalonic acid diester derivative of the general formula (III),

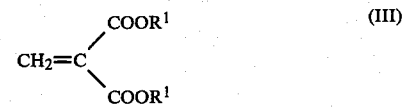

wherein $R^1$ is as defined above, subjecting the resulting product to catalytic hydrogenation, treating the resulting product with an alkali, and reacting the resulting octahydroindoloquinolisine monoester derivative with a nitrosating agent in an acidic medium.

8 Claims, No Drawings

PROCESS FOR THE PREPARATION OF HYDROXYAMINO-EBURNANE DERIVATIVES AND OCTAHYDROINDOLOQUINOLIZINE INTERMEDIATES

The invention relates to new hydroxyamino-eburnane derivatives of the formula (I),

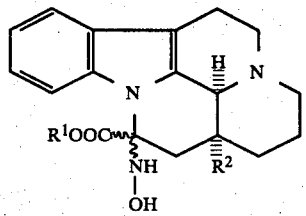

(I)

wherein $R^1$ and $R^2$ are each $C_{1-6}$ alkyl, as well as to pharmaceutically acceptable acid addition salts and optically active isomers of these compounds.

The new compounds are prepared according to the invention in the following manner:

(A) a hexahydroindoloquinolizinium derivative of the formula (II),

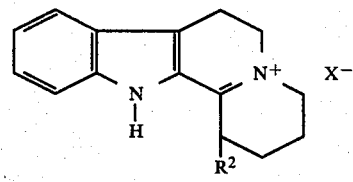

(II)

wherein X is an acid residue, is reacted, optionally in the presence of a basic catalyst, with a methylenemalonic acid diester derivative of the formula (III),

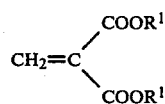

(III)

(B) the resulting new hexahydroindoloquinolizinium ester derivative of the formula (IVa) and/or (IVb),

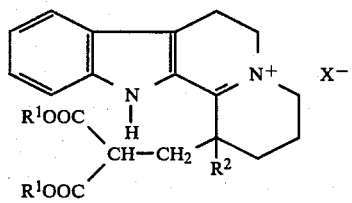

(IVa)

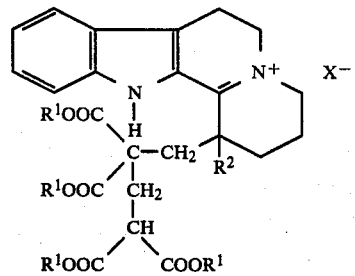

(IVb)

wherein $R^1$, $R^2$ and X are as defined above, is subjected to catalytic hydrogenation; the resulting new octahydroindoloquinolizine ester derivative of the formula (Va) and/or (Vb),

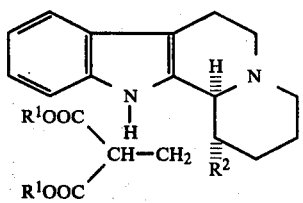

(Va)

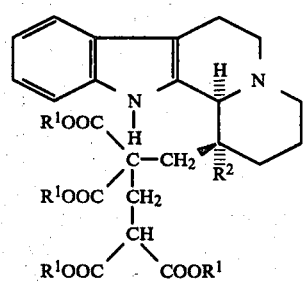

(Vb)

wherein $R^1$ and $R^2$ are as defined above, is treated with an alkali; and the resulting new octahydroindoloquinolizine monoester derivative of the formula (VII),

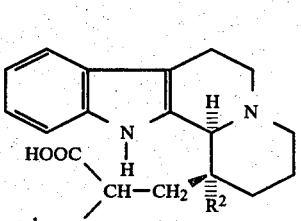

(VII)

wherein $R^1$ and $R^2$ are as defined above, is reacted with a nitrosating agent in an acidic medium. If desired, the compounds of the formulae (IVa) and (IVb) obtained as intermediates in the synthesis are converted into the respective free base, the compounds of the formulae (Va), (Vb), (VII) and (I) are converted into their salts and/or are resolved, and the subsequent reaction steps are performed optionally with the appropriate optically active isomers.

In the compounds of the formula (I) $R^1$ and $R^2$ can represent methyl, ethyl, n-propyl, isopropyl, n-butyl, sec.-butyl, tert.-butyl, n-pentyl, isopentyl, n-hexyl or isohexyl.

The new compounds of the formula (I) are valuable intermediates of the synthesis of compounds with excellent pharmaceutical effects. Thus when a compound of the formula (I) is treated with a dilute aqueous acid, a mixture of the corresponding vincaminic acid ester and apovincaminic acid ester is formed. These compounds can be separated from each other by fractional crystallization, and, if desired, converted into other esters. Thus the compounds of the formula (I) can be converted either into vincamine, a substance of valuable pharmaceutical effects, or into apovincaminic acid ethyl ester (Cavinton®), a substance even more effective than vincamine, or both pharmaceutically active compounds can be prepared simultaneously from the appropriate compound of the formula (I) (see Hungarian patent application No. RI-634).

Moreover, the compounds of the formula (I) also possess valuable pharmacological effects, i.e. they increase the blood flow of the limbs.

The compounds of the formula (II) utilized as starting substances in the process of the invention, wherein $R^2$ is $C_{1-6}$ alkyl and X is an acid residue, can be prepared as described in J. Am. Chem. Soc. 87, 1580–1589.

The reactants of the formula (III) can be prepared as described in J. Org. Chem. 4, 493 (1939) e.g. by reacting a malonic acid ester with paraformaldehyde.

The reaction of the compounds of the formulae (II) and (III) is performed in an inert organic solvent. As inert organic solvent, a hydrocarbon, a halogenated hydrocarbon, an alcohol, acetonitrile and the like can be used.

Halogenated hydrocarbons, such as dichloromethane and chloroform, and $C_{1-6}$ aliphatic alcohols, such as tert.-butanol, have proved to be particularly preferred.

The reaction is performed optionally in the presence of a basic catalyst, such as an aliphatic or cyclic organic amine (e.g. diethylamine, triethylamine, piperidine or pyridine). Catalytic amounts of an alkali metal alcoholate, such as potassium tert.-butoxide, can also be used for the same purpose. The reaction is performed preferably at room temperature. Depending on the temperature, the reaction time varies from some hours to some days.

The relative amounts of the compounds of the formulae (IVa) and (IVb) formed in this step depend on the amount of the reactant of the formula (III) used. When the reactant of the formula (III) is used in a large excess, a compound of the formula (IVc),

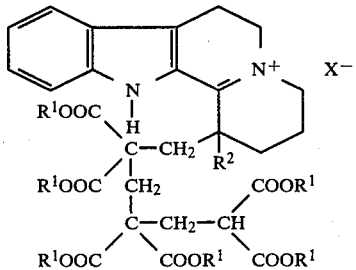

(IVc)

wherein $R^1$, $R^2$ and X are as defined above, also forms in smaller amount in addition to the compounds of the formulae (IVa) and (IVb). In practice it is, however, not recommended to use the reactant of the formula (III) in too large excess.

The intermediates of the formulae (IVa), (IVb) and (IVc) are new, and also possess biological activities. The compounds of the formulae (IVa), (IVb) and (IVc) can be converted into the free bases in a manner known per se, by treating the salts with an alkali. The scope of the invention also extends to the preparation of the free bases. Although the next step of the synthesis can also be performed with the free bases, it is preferred to utilize the acid addition salts of the formulae (IVa) and/or (IVb) as starting substances in the catalytic hydrogenation.

In the next step of the synthesis the compounds of the formulae (IVa) and/or (IVb) are subjected to catalytic hydrogenation. Metals capable of hydrogen transfer, such as palladium, platinum, nickel, iron, copper, cobalt, chromium, zinc, molybdenum or tungsten, or metal oxides and sulfides of these metals can equally be used as hydrogenating catalysts.

Supported catalysts may also be used in the hydrogenation step; the supports preferably are carbon (primarily activated carbon), silicon dioxide, alkaline-earth-metal sulfates and alkaline-earth-metal carbonates.

Most frequently palladium-on-activated carbon or Raney-nickel is used as catalyst, but the catalyst should always be selected on the basis of the nature of the substance to be hydrogenated and the reaction conditions. Catalytic hydrogenation is performed in an inert solvent in which the starting substance is highly soluble, such as water, $C_{1-6}$ aliphatic alcohols, halogenated $C_{1-6}$ aliphatic hydrocarbons, ethyl acetate, dioxane, glacial acetic acid or mixtures thereof. If platinum oxide is used as the catalyst, hydrogenation is performed preferably in a neutral or slightly acidic medium, whereas if Raney-nickel is utilized, it is preferred to conduct the reaction in a neutral medium.

Depending on the nature of the starting substance and other reaction parameters (time and pressure), the temperature of the reaction may vary over a wide range. Catalytic hydrogenation is performed preferably at room temperature and under atmospheric pressure until the uptake of the calculated amount of hydrogen signals termination.

When a single compound of the formula (IVa) or (IVb) is hydrogenated, a single compound of the formula (Va) or (Vb) is obtained, whereas when a mixture of the compounds of the formulae (IVa) and (IVb) is hydrogenated, the respective mixture of the compounds of the formulae (Va) and (Vb) is formed. If the mixture subjected to hydrogenation also contains a compound of the formula (IVc), one also obtains the corresponding reduced substance of the formula (Vc),

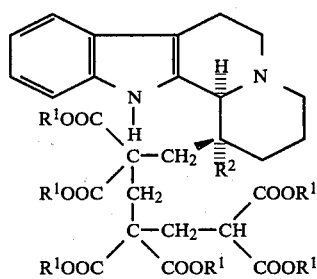

(Vc)

wherein $R^1$ and $R^2$ are as defined above, in the reaction product beside the compounds of the formulae (Va) and (Vb).

The intermediates of the formulae (Va), (Vb) and (Vc) are new and biologically active. If desired, these compounds can be converted into their acid-addition salts utilizing e.g. the acids listed below in connection with the preparation of the salts of the end-products, or, if desired, the racemic compounds can be resolved in a manner known per se. The scope of the invention embraces both the acid-addition salts and the optically active isomers of the compounds having the formulae (Va), (Vb) and (Vc).

Upon neutralization of the mother liquor obtained in the catalytic hydrogenation, and subjecting it to preparative layer chromatography, a compound of the formula (VI),

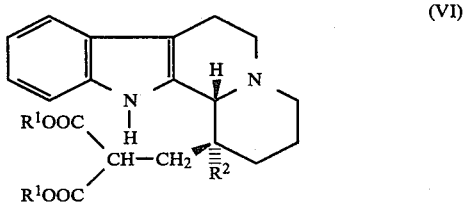

wherein $R^1$ and $R^2$ are as defined above, can also be isolated in a rather small amount. The compound of the formula (VI) is a structural isomer of the compound of the formula (Va); in the compounds of the formula (Va) the hydrogen is attached in position $\alpha$ to the 12b carbon atom and thus it is in cis position related to substituent $R^2$, whereas in the compounds of the general formula (VI) the hydrogen is attached in position $\beta$ to the 12b carbon atom and thus its relative position to substituent $R^2$ is trans. This also proves unambiguously that subjecting a compound of the formula (IVa) or (IVb) to catalytic hydrogenation results in, a stereoselective reduction and the respective cis compound of the formula (Va) or (Vb) is obtained.

In the next step of the synthesis the compounds of the formulae (Va) and/or (Vb) are treated with an alkali. For this purpose an inorganic base, preferably an alkali metal hydroxide, such as potassium or sodium hydroxide, can be used. The reaction is performed in an inert organic solvent or in a mixture of such solvents. As organic solvent it is preferred to use an alcohol $R^1OH$ whose organic moiety corresponds to that of group $R^1O$— of the starting substance. The reaction can be performed at any temperature between room temperature and the boiling point of the reaction mixture. Depending on the temperature used, the reaction proceeds within 10 minutes and 1.5 hours.

Any of the compounds of the formulae (Va), (Vb) and (Vc) and any mixtures thereof yield the same hemiester of the formula (VII) upon treatment with an alkali. When a compound of the formula (Vb) is used as starting substance, it first transforms into the corresponding compound of the formula (Va) upon the effect of the alkali. The reaction can be monitored by thin layer chromatography, and, if desired, it can be interrupted at an appropriate stage to separate the compound of the formula (Va) from the mixture. The resulting compound of the formula (Va) is indentical to that obtained by hydrogenating a compound of the formula (IVa) or a mixture of the compounds of the formulae (IVa) and (IVb).

The compounds of the formula (VII) are new and biologically active. If desired, these compounds can be converted into their acid-addition salts, or the racemic compounds can be resolved according to known techniques. The scope of the invention also embraces the salts and optically active isomers of the compounds having the formula (VII).

In the last step of the synthesis according to the invention a compound of the formula (VII) is subjected to nitrosation in acidic medium. This reaction can be performed with an alkali nitrite, such as potassium or sodium nitrite, in glacial acetic acid. Alternatively, the compound of the formula (VII) can be nitrosated with a $C_{1-6}$ alkylnitrite, preferably tert.-butylnitrite or amylnitrite, in an inert organic solvent, preferably in a halogenated $C_{1-6}$ aliphatic hydrocarbon (such as dichloromethane), in the presence of an acid dissolved in some drops of a $C_{1-6}$ aliphatic alcohol, preferably in the presence of ethanolic hydrochloric acid.

The four-step synthesis according to the invention can also be performed in a single series of operations, without isolating, crystallizing and identifying the intermediates formed.

The reaction mixtures obtained in any step of the process according to the invention can be processed in a manner known per se, depending on the nature of the starting substances, end-products, solvents, etc. If the product separates from the mixture at the end of the reaction, it can be isolated by filtration. If the product remains in solution, the reaction may be filtered in order to remove the solid by-products eventually formed, and then the filtrate can be evaporated in vacuo, or the product can be precipitated from the filtrate by an appropriate solvent. The bases can also be isolated in the form of their acid-addition salts so that an appropriate acid or a solution thereof is added to the solution containing the base. Dissolved compounds can also be isolated from their solutions by preparative thin layer chromatography.

The processing of the reaction mixtures obtained in the intermediate steps of the synthesis generally yields the intermediates in crystalline form. If the resulting substance is an amorphous powder or an oil, it can be crystallized generally easily in common solvents selected in accordance with the solubility of the intermediate in question.

If desired, any of the intermediates or the end-product can be subjected to further purification, such as recrystallization, etc.

The compounds of the formula (I) can be converted into their pharmaceutically acceptable acid-addition salts by reacting them with the appropriate acids.

Of the acids used for salt formation the following are to be mentioned: mineral acids, such as hydrohalic acids (e.g. hydrochloric acid, hydrobromic acid), sulfuric acid, phosphoric acid, nitric acid, perchloric acid, etc.; organic carboxylic acids, such as formic acid, acetic acid, propionic acid, glycolic acid, maleic acid, hydroxymaleic acid, fumaric acid, salicylic acid, lactic acid, cinnamic acid, benzoic acid, phenylacetic acid, p-aminobenzoic acid, p-hydroxybenzoic acid, p-aminosalicylic acid, etc.; alkylsulfonic acids, such as methanesulfonic acid, ethanesulfonic acid, etc.; cycloaliphatic sulfonic acids, such as cyclohexylsulfonic acid; arylsulfonic acids, such as p-toluenesulfonic acid, naphthylsulfonic acid, sulfanilic acid, etc.; amino acids, such as aspartic acid, glutamic acid, etc.

The new compounds of the formula (I) possess vasodilatating effects, and act primarily on the circulation of the limbs.

The pharmacological tests were performed on dogs anaesthetized with chloralose urethane. The test substance was administered intravenously as an aqueous solution in a dosage of 1 mg/kg body weight, and the arterial blood pressure, pulse rate and arterial blood flow were measured. The latter measurement was performed on the arteria femoralis and on the arteria carotis interna. The resistance of these vessel systems was calculated from the values obtained by the formula $$\text{vascular resistance} = \frac{\text{blood pressure}}{\text{blood flow in the vessel examined}}$$

The results are listed in Tables 1 and 2. The abbreviations have the following meanings:
MABP = medium arterial blood pressure
PR = pulse rate
CBF = blood flow in the carotis interna
CVR = carotis vascular resistance
FBF = blood flow in the arteria femoralis
FVR = femoral vascular resistance

TABLE 1

Circulation influencing effects of 1 mg/kg of (±)-cis-14-methoxycarbonyl-14-hydroxyamino-eburnane (3αH,16αEt), prepared according to Example 9 (average ± standard error)

| Time (min.)* | 0 | 1 | 3 | 5 | 20 |
|---|---|---|---|---|---|
| MABP mm Hg | 132 ± 9.3 | 118 ± 7.9 | 124 ± 6.2 | 126 ± 6.8 | 132 ± 7.8 |
| % | | −10.2 | −5.8 | −4.1 | 0 |
| PR min$^{-1}$ | 149 ± 10.9 | 161 ± 15.8 | 158 ± 15.5 | 156 ± 17.7 | 148 ± 13.9 |
| % | | +7.7 | +5.7 | +4.1 | −0.9 |
| CBF ml.min$^{-1}$ | 49 ± 13.0 | 61 ± 20.2 | 55 ± 17.6 | 55 ± 16.0 | 49 ± 13.0 |
| % | | +20.5 | +8.9 | +9.0 | 0 |
| CVR mm Hg.min.ml$^{-1}$ | 3.1 ± 0.6 | 2.4 ± 0.5 | 2.8 ± 0.6 | 2.8 ± 0.6 | 3.1 ± 0.6 |
| % | | −25 | −12 | −11 | +1.3 |
| FBF ml.min$^{-1}$ | 72 ± 18.8 | 117 ± 29.1 | 81 ± 25.1 | 77 ± 22.2 | 70 ± 17.9 |
| % | | +71 | +9.5 | +5.8 | −3.4 |
| FVR mm Hg.min.ml$^{-1}$ | 2.3 ± 0.7 | 1.2 ± 0.2 | 2.0 ± 0.6 | 2.1 ± 0.7 | 2.5 ± 0.8 |
| % | | −45 | −13 | −7.8 | +3.9 |

*Determined before treatment (0) and 1, 3, 5 and 20 minutes after the treatment

TABLE 2

Maximum percentage effects of (±)-cis-14-methoxycarbonyl-14-hydroxyamino-eburnane (3aH,16αEt) in the individual tests

| | Number of the dog used | | | | Average ± |
|---|---|---|---|---|---|
| Test | 247 | 256 | 259 | 263 | standard error |
| MABP | −11 | −15 | 0 | −5 | −10.2 ± 2.3* |
| PR | 0 | +9 | +14 | +8 | +7.7 ± 3.0 |
| CBF | +38 | +25 | +14 | +5 | +20.5 ± 7.3 |
| CVR | −34 | −32 | −22 | −13 | −25 ± 5.5* |
| FBF | +116 | +57 | +67 | +44 | +71 ± 15.9* |
| FVR | −58 | −43 | −46 | −32 | −44.7 ± 5.3* |

*Statistically significant average (P < 0.05)

The data of the tables demonstrate that the compound, when administered in an intravenous dosage of 1 mg/kg body weight, provokes a temporary and slight decrease in blood pressure and increases the pulse rate. The main effect of the compound resides in the increase of the blood flow in the two vessel systems investigated. This effect is particularly significant on the limb vessels (71%), which is a consequence of an about 45% dilatation in the vessels concerned. Simultaneously, a dilatation of 25% can be observed on the carotis vessel system, which results in a 20% increase in the blood flow.

The new compounds of the general formula (I) and pharmaceutically acceptable acid addition salts thereof can be converted into pharmaceutical compositions by admixing them with non-toxic, inert, solid or liquid carriers and/or auxiliary agents commonly applied in the preparation of compositions for enteral or parenteral administration. As carrier e.g. water, gelatine, lacetose, starch, pectin, magnesium stearate, stearic acid, talc, vegetable oils (such as peanut oil, olive oil), etc. can be applied.

The pharmaceutical compositions can be presented in conventional forms, such as in the form of solid (e.g. round or edged tablets, coated tablets, capsules, pills, suppositories, etc.) or liquid preparations (e.g. oily or aqueous solutions, suspensions, emulsions, syrups, soft gelatine capsules, injectable oily or aqueous solutions or suspensions, etc.). The amount of the solid carrier may vary within wide limits; a dosage unit may contain preferably about 25 to 1000 mg of a solid carrier. If desired, conventional pharmaceutical additives, such as preservatives, stabilizing agents, wetting agents, emulsifying agents, salts for adjusting the osmotic pressure, buffers, flavoring agents, odorants, etc. can also be added to the pharmaceutical compositions. Beside the new compounds of the formula (I), the pharmaceutical compositions may also contain other known and therapeutically active agents.

The pharmaceutical compositions are presented preferably in the form of unit dosages, and they are prepared according to conventional methods, such as by sieving, blending, granulating and pressing or dissolving the active agents and other ingredients. If necessary, the compositions can be subjected to other pharmacotechnological operations, such as sterilization, etc.

The invention is elucidated in detail by the aid of the following non-limiting Examples.

EXAMPLE 1

(±)-1α-Ethyl-1β-(2',2'-diethoxycarbonylethyl)-1,2,3,4,6,7,12,12bα-octahydro-indolo[2,3-a]quinolizine and (±)-1α-ethyl-1β-(2',2',4',4'-tetraethoxycarbonyl-butyl)-1,2,3,4,6,7,12,12bα-octahydro-indolo[2,3-a]quinolizine A solution of 8.0 ml (8.4 g, 48.8 mmoles) of methylenemalonic acid diethyl ester in 10 ml of dichloromethane is added to a stirred suspension of 10.00 g (28.4 mmoles) of 1-ethyl-1,2,3,4,6,7-hexahydro-12H-indolo[2,3-a]quinolizin-5-ium-perchlorate in 60 ml of dichloromethane and 3.6 ml (2.60 g, 25.7 mmoles) of triethylamine. The reaction mixture is allowed to stand for 2 days at room temperature.

The solvent is evaporated in vacuo, and the residual orange red oil is triturated thrice with 30 ml of ether, each, and thrice with 30 ml of petroleum ether, each.

18 g of a mixture of 1-ethyl-1-(2',2'-diethoxycarbonylethyl)-1,2,3,4,6,7-hexahydro-12H-indolo[2,3- a]quinolizin-5-ium perchlorate and 1-ethyl-1-(2',2',4',4'-tetraethoxycarbonyl-butyl)-1,2,3,4,6,7-hexahydro-12H-indolo[2,3-a]quinolizin-5-ium perchlorate are obtained as an oily substance. This mixture is utilized directly, i.e. without purification, in the next step of the synthesis.

IR (KBr): 3260 (indole NH), 1735, 1715 (CO), 1615 and 1520 (C=N) cm$^{-1}$.

The oily mixture (18 g) obtained as described above is dissolved in a mixture of 200 ml of ethanol and 50 ml of dichloromethane, and the mixture is hydrogenated in the presence of 8 g of a pre-hydrogenated 10% palladium-on-carbon catalyst. After the uptake of the required amount of hydrogen the catalyst is filtered off and washed thrice with 3 ml of ethanol, each, and then thrice with 30 ml of dichloromethane, each. The filtrate and the wash are combined, evaporated to dryness in vacuo, and the residue is crystallized from 50 ml of ethanol. The separated substance is filtered off, washed with ethanol and dried.

9.0 g of (±)-1α-ethyl-1β-(2',2',4',4'-tetraethoxycarbonyl-butyl)-1,2,3,4,6,7,12,12bα-octahydro-indolo[2,3-a]quinolizine perchlorate are obtained, which corresponds to a yield of 45.3% calculated for 1-ethyl-1,2,3,4,6,7-hexahydro-12H-indolo[2,3-a]quinolizine-5-ium perchlorate.

The product melts at 216°–218° C. after crystallization from ethanol.

Analysis: calculated for C$_{33}$H$_{46}$N$_2$O$_8$.HClO$_4$ (mol.wt.: 699.18): C: 56.68%, H: 6.63%, N: 4.01%; found: C: 57.00%, H: 6.55%, N: 4.10%.

(±)-1α-Ethyl-1β-(2',2',4',4'-tetraethoxycarbonyl-butyl)-1,2,3,4,6,7,12,12bα-octahydro-indolo[2,3-a]quinolizine hydrochloride melts at 211°–212° C. (from ethanol).

Mass spectrum (m/e, %): 426 (M+ −172; 6), 425 (3), 411 (0.3), 397 (0.3), 381 (2), 353 (1), 267 (100), 253 (3), 237 (5), 197 (8), 185 (6), 184 (6), 170 (10), 169 (10), 156 (6), 144 (5), 127 (10), 99 (10).

(±)-1α-Ethyl-1β-(2',2',4',4'-tetraethoxycarbonyl-butyl)-1,2,3,4,6,7,12,12bα-octahydro-indolo[2,3-a]quinolizine base can be prepared by dissolving either the hydrochloride or the perchlorate in dichloromethane, shaking the solution with an 5% aqueous sodium carbonate solution, separating the organic phase, drying it over anhydrous magnesium sulfate, filtering, and evaporating the filtrate in vacuo.

$^1$H-NMR (CDCl$_3$, δ): 7.86 (1H, indole NH), 4.30–3.85 (8H, m, OCH$_2$), 1.45–1.0 (15H, m, CH$_2$-CH$_3$) ppm.

Ethanol is distilled off from the ethanolic mother liquor obtained after the removal of (±)-1α-ethyl-1β-(2',2',4',4'-tetraethoxycarbonyl-butyl)-1,2,3,4,6,7,12,12bα-octahydro-indolo[2,3-a]quinolizine perchlorate, the residue is dissolved in 30 ml of dichloromethane, and the solution is shaken with 20 ml of a 5% aqueous sodium carbonate solution. The organic phase is separated, dried over anhydrous magnesium sulfate, filtered, and the filtrate is evaporated to dryness in vacuo. The residue is dissolved in 10 ml of ethanol, and the solution is acidified to pH 5 with ethanolic hydrochloric acid. The hydrochloride is precipitated from the soluton with 10 ml of ether, the solid is filtered off, washed with ether and dried.

4.0 g of (±)-1α-ethyl-1β-(2',2'-diethoxycarbonylethyl)-1,2,3,4,6,7,12,12bα-octahydro-indolo[2,3-a]quinolizine hydrochloride are obtained, which corresponds to a yield of 30.4% calculated for 1-ethyl-1,2,3,4,6,7-hexahydro-12H-indolo[2,3-a]quinolizin-5-ium perchlorate.

The product melts at 202°–204° C. (from ether).

IR (KBr): 3300 (indole NH), 1720 (CO) cm$^{-1}$.

Mass spectrum (m/e, %): 426 (M+, 15), 425 (12), 411 (1), 397 (1), 381 (8), 365 (0.5), 353 (2), 307 (0.6), 267 (100), 253 (2), 237 (4), 197 (12), 185 (8), 184 (7), 170 (10), 169 (12), 156 (5), 145 (0.6), 144 (5), 143 (3), 127 (1), 124 (3).

(±)-1α-Ethyl-1β-(2',2'-diethoxycarbonylethyl)-1,2,3,4,6,7,12,12bα-octahydro-indolo[2,3-a]quinolizine base is prepared by dissolving the hydrochloride in dichloromethane, shaking the solution with a 5% aqueous sodium carbonate solution, separating the organic phase, drying it over anhydrous magnesium sulfate, filtering, and evaporating the filtrate to dryness.

$^1$H-NMR (CDCl$_3$, δ): 7.82 (1H, indole NH), 7.2–6.85 (4H, m, aromatic protons), 3.90 (4H, q, J=7.3 cps, O-CH$_2$), 1.2–0.8 (9H, m, —CH$_3$) ppm.

(±)-1α-Ethyl-1β-(2',2'-diethoxycarbonylethyl)-1,2,3,4,6,7,12,12bα-octahydro-indolo[2,3-a]quinolizine base, obtained as described above, is subjected to preparative layer chromatography on a KG-60 PF$_{254+366}$ grade silica gel plate, applying a 14:3 mixture of benzene and methanol as solvent and acetone as eluting agent. After evaporating the eluate and crystallizing the residue from ethanol, a substance of higher R$_f$ value is isolated.

In this way 0.25 g of (±)-1α-ethyl-1β-(2',2'-diethoxycarbonylethyl)-1,2,3,4,6,7,12,12bβ-octahydro-indolo[2,3-a]quinolizin are obtained, which corresponds to a yield of 2% calculated for 1-ethyl-1,2,3,4,6,7-hexahydro-12H-indolo[2,3-a]quinolizine-5-ium perchlorate.

M.p.: 127°–128° C. (from ethanol).

IR (KBr): 3280 (indole NH), 1730, 1705 (CO) cm$^{-1}$.

Mass spectrum (m/e, %): 426 (M+, 13), 425 (7.1), 411 (0.8), 397 (0.8), 381 (4.2), 366 (0.9), 353 (1.8), 337 (0.8), 335 (0.5), 307 (0.6), 267 (100).

EXAMPLE 2

(±)-1α-Ethyl-1β-(2',2'-diethoxycarbonylethyl)-1,2,3,4,6,7,12,12bα-octahydro-indolo[2,3-a]quinolizine
and
(±)-1α-ethyl-1β-(2',2',4',4'-tetraethoxycarbonyl-butyl)-1,2,3,4,6,7,12,12bα-octahydro-indolo[2,3-a]quinolizine A solution of 3.03 ml (3.12 g, 18.4 mmoles) of methylenemalonic acid diethyl ester in 5 ml of dichloromethane is added to a stirred suspension of 5.00 g (14.2 mmoles) of 1-ethyl-1,2,3,4,6,7-hexahydro-12H-indolo[2,3-a]quinolizin-5-ium perchlorate in 30 ml of dichloromethane and 0.080 g (0.715 mmoles) of potassium tert.-butoxide. The reaction mixture is allowed to stand at room temperature for one day.

Thereafter the solvent is evaporated in vacuo, and the orange-red oily residue is triturated thrice with 5 ml of petroleum ether, each.

9 g of a mixture of 1-ethyl-1-(2',2'-diethoxycarbonylethyl)-1,2,3,4,6,7-hexahydro-12H-indolo[2,3-a]quinolizin-5-ium perchlorate and 1-ethyl-1-(2',2',4',4'-tetraethoxycarbonyl-butyl)-1,2,3,4,6,7-hexahydro-12H-indolo[2,3-a]quinolizin-5-ium perchlorate are obtained as an oily substance. This mixture is applied directly, i.e. without purification, in the next step of the synthesis.

IR (KBr): 3260 (indole NH), 1735, 1715 (CO), 1615, 1520 (C=N) cm$^{-1}$.

The oily residue (9 g) obtained as described above is dissolved in a mixture of 10 ml of ethanol and 25 ml of dichloromethane, and the solution is hydrogenated in the presence of 6 g of a pre-hydrogenated 10% palladium-on-carbon catalyst. After the uptake of the required amount of hydrogen the catalyst is filtered off and washed thrice with 3 ml of ethanol, each, and then thrice with 10 ml of dichloromethane, each. The filtrate and the wash are combined, evaporated to dryness in vacuo, and the residue is crystallized from 30 ml of ethanol. The separated substance is filtered off, washed with ethanol, and dried.

8.0 g of a mixture of (±)-1α-ethyl-1β-(2',2',4',4'-tetraethoxycarbonyl-butyl)-1,2,3,4,6,7,12,12bα-octahydro-indolo[2,3-a]quinolizine perchlorate and (±)-1α-ethyl-1β-(2',2'-diethoxycarbonylethyl)-1,2,3,4,6,7,12,12bα-octahydro-indolo[2,3-a]quinolizine perchlorate are obtained; m.p.: 181°–185° C.

This salt mixture can be used in the next step of the synthesis directly in the ethanol-dichloromethane solution obtained after filtering off the catalyst.

In order to determine the composition of the perchlorate salt mixture 0.8 g of the mixture are dissolved in 6 ml of dichloromethane, the solution is shaken with 4 ml of a 5% aqueous sodium carbonate solution, the organic phase is separated, dried over anhydrous magnesium sulfate, filtered, and the filtrate is evaporated to dryness in vacuo. The residue is subjected to preparative layer chromatography (adsorbent: aluminum oxide Typ-T; solvent: 3:1 mixture of dichloromethane and benzene; eluting agent: 20:1 mixture of dichloromethane and methanol).

The substance with higher $R_f$ value is dissolved in 1.2 ml of ethanol, and the solution is acidified to pH 5 with ethanolic hydrochloric acid. The hydrochloride is precipitated with 1.2 ml of ether, filtered off, washed with ether and dried.

0.46 g of (±)-1α-ethyl-1β-(2',2'-diethoxycarbonylethyl)-1,2,3,4,6,7,12,12bα-octahydro-indolo[2,3-a]quinolizine hydrochloride are obtained, which corresponds to a yield of 70.5%. M.p.: 202°–204° C. (from ethanol and ether).

The substance with lower $R_f$ value is converted into the perchlorate with 70% aqueous perchloric acid solution, and the salt is crystallized from ethanol.

0.26 g of (±)-1α-ethyl-1β-(2',2',4',4'-tetraethoxycarbonyl-butyl)-1,2,3,4,6,7,12,12bα-octahydro-indolo[2,3-a]quinolizine perchlorate are obtained, which corresponds to a yield of 26%. M.p.: 216°–218° C. (from ethanol).

EXAMPLE 3

(±)-1α-Ethyl-1β-(2',2'-diethoxycarbonylethyl)-1,2,3,4,6,7,12,12bα-octahydro-indolo[2,3-a]quinolizine 600 mg (1 mmole) of (±)-1α-ethyl-1β-(2',2',4',4',-tetraethoxycarbonyl-butyl)-1,2,3,4,6,7,12,12bα-octahydro-indolo[2,3a]quinolisine, prepared as described in Example 1 or 2, are dissolved in 8 ml of ethanol, and a solution of 120 mg of potassium hydroxide in 1 ml of water and 1 ml of ethanol is added. As indicated by thin layer chromatography using aluminum oxide (Typ-T) as adsorbent and a 3:1 mixture of dichloromethane and benzene as solvent, the reaction proceeds at room temperature within 20 minutes. In this system the $R_f$ value of (±)-1α-ethyl-1β-(2',2'-diethoxycarbonylethyl)-1,2,3,4,6,7,12,12bα-octahydro-indolo[2,3a]quinolizine is higher than that of (±)-1α-ethyl-1β-(2',2',4',4'-tetraethoxycarbonyl-butyl)-1,2,3,4,6,7,12,12bα-octahydro-indolo[2,3-a]quinolizine. The reaction mixture is neutralized to pH 6 with acetic acid, and the solvent is distilled off in vacuo. The residue is dissolved in 3 ml of water, the solution is rendered alkaline (pH=9) with an 5% aqueous sodium carbonate solution, and then extracted thrice with 5 ml of dichloromethane, each. The organic solutions are combined, dried over anhydrous magnesium sulfate, filtered, and the solvent is evaporated in vacuo. The oily residue is dissolved in 3 ml of ethanol, ethanolic hydrochloric acid is added to the solution, and the hydrochloride thus formed is crystallized with ether.

0.25 g of (±)-1α-ethyl-1β-(2',2'-diethoxycarbonylethyl)-1,2,3,4,6,7,12,12bα-octahydro-indolo[2,3-a]quinolizine hydrochloride are obtained, which corresponds to a yield of 53%.

M.p.: 201°–204° C. (from ether).

IR (KBr): 3300 (indole NH), 1720 (CO) cm$^{-1}$.

EXAMPLE 4

(±)-1α-Ethyl-1β-(2'-carboxy-2'-ethoxycarbonylethyl)-1,2,3,4,6,7,12,12bα-octahydro-indolo[2,3-a]quinolizine A solution of 0.067 g (1.2 mmoles) of potassium hydroxide in 0.3 ml of water and 0.9 ml of ethanol is added to a solution of 0.46 g (1.08 mmoles) of (±)-1α-ethyl-1β-(2',2',-diethoxycarbonylethyl)-1,2,3,4,6,7,12,12bα-octahydro-indolo[2,3-a]quinolizine, prepared as described in Example 1 or 2, in 3 ml of ethanol. The reaction mixture is boiled on a steam bath for 1.5 hours. Thereafter the solvent is evaporated in vacuo, the oily residue is dissolved in 3 ml of water, and the aqueous solution is extracted twice with 2 ml of ether, each. The aqueous phase is neutralized to pH 6 with acetic acid. The separated white, crystalline substance is filtered off, washed with 5 ml of water, and dried.

0.32 g of (±)-1α-ethyl-1β-(2'-carboxy-2'-ethoxycarbonylethyl)-1,2,3,4,6,7,12,12bα-octahydro-indolo[2,3-a]quinolizine are obtained, which corresponds to a yield of 74%. M.p.: 113°–115° C. (from water).

When subjected to thin layer chromatography on KG-G silica gel plate, utilizing a mixture of 15 ml of benzene, 5 ml of methanol and 2 drops of concentrated aqueous ammonia as solvent, the $R_f$ value of 1α-ethyl-1β-(2',2'-diethoxycarbonylethyl)-1,2,3,4,6,7,12,12bα-octahydro-indolo[2,3-a]quinolizine is higher than that of (±)-1α-ethyl-1β-(2'-carboxy-2'-ethoxycarbonylethyl)-1,2,3,4,6,7,12,12bα-octahydro-indolo[2,3-a]quinolizine.

IR (KBr): 3360 (indole NH), 1715 (CO), 1600 (COO$^-$) cm$^{-1}$.

Mass spectrum (m/e, %): 354 (M$^+$ −44; 53), 353 (58), 339 (8), 325 (0.3), 309 (12), 281 (2), 267 (100), . . . 44 (1000).

EXAMPLE 5

(±)-1α-Ethyl-1β-(2'-carboxy-2'-ethoxycarbonylethyl)-1,2,3,4,6,7,12,12bα-octahydro-indolo[2,3-a]quinolizine A solution of 0.092 g (1.64 mmoles) of potassium hydroxide in 0.3 ml of water and 0.9 ml of ethanol is added to a solution of 0.428 g (0.715 mmoles) of (±)-1α-ethyl-1β-(2',2',4',4'-tetraethoxycarbonyl-butyl)-1,2,3,4,6,7,12,12bα-octahydro-indolo[2,3-a]quinolizine, prepared as described in Example 1 or 2, in 3 ml of ethanol. The reaction mixture is boiled on a steam bath for 0.75 hours. Thereafter the solvent is evaporated in vacuo, the oily residue is dissolved in 3 ml of water, and the resulting solution is washed twice with 2 ml of ether, each. The aqueous solution is neutralized to pH 6 with acetic acid, the separated white, crystalline substance is filtered off, washed with 5 ml of water, and dried.

0.24 g of (±)-1α-ethyl-1β-(2'-carboxy-2'-ethoxycarbonyl-ethyl)-1,2,3,4,6,7,12,12bα-octahydro-indolo[2,3-a]quinolizine are obtained, which corresponds to a yield of 74%. M.p.: 112°–114° C.

EXAMPLE 6

(±)-1α-Ethyl-1β-(2'-carboxy-2'-ethoxycarbonyl-ethyl)-1,2,3,4,6,7,12,12bα-octahydro-indolo[2,3-a]quinolizine The filtrate obtained in Example 2 after removing the catalyst from the reaction mixture, which is an ethanol-dichloromethane solution of (±)-1α-ethyl-1β-(2',2'-diethoxycarbonylethyl)-1,2,3,4,6,7,12,12bα-octahydro-indolo[2,3-a]quinolizine perchlorate and (±)-1α-ethyl-1β-(2',2',4',4'-tetraethoxycarbonyl-butyl)-1,2,3,4,6,7,12,12bα-octahydro-indolo[2,3-a]quinolizine perchlorate and contains the two salts in a weight ratio of about 3:1, is applied as starting substance.

The solvent is evaporated in vacuo, and the oily salt mixture obtained as residue is dissolved in 50 ml of dichloromethane. 30 ml of a 5% aqueous sodium carbonate solution are added, the mixture is shaken, the organic phase is separated, dried over anhydrous magnesium sulfate, filtered, and the filtrate is evaporated to dryness in vacuo. 1.54 g of the oily residue, which is a mixture of 2.34 mmoles of the diethoxy base and 0.90 mmoles of the tetraethoxy base, are dissolved in 16 ml of ethanol, and a solution of 0.24 g (4.28 mmoles) of potassium hydroxide in 2 ml of water is added. The reaction mixture is boiled for 1 to 1.5 hours on a steam bath. Thereafter the solvent is evaporated in vacuo, the residue is dissolved in 10 ml of water, and this alkaline solution is extracted thrice with 10 ml of ether, each. The organic extracts are combined, dried over anhydrous magnesium sulfate, filtered, and the filtrate is evaporated. 0.4 g of an oily substance is obtained as a residue, which consists mainly of the starting compound mixture. The pH of the aqueous phase is adjusted to 6 with acetic acid, and the separated organic substance is extracted four times with 15 ml of dichloromethane, each. The organic extracts are combined, dried over anhydrous magnesium sulfate, filtered, and the filtrate is evaporated in vacuo. The oily residue is triturated with 10 ml of ether, the separated substance is filtered off, washed with 5 ml of ether, and dried.

0.76 g of (±)-1α-ethyl-1β-(2'-carboxy-2'-ethoxycarbonylethyl)-1,2,3,4,6,7,12,12bα-octahydro-indolo[2,3-a]quinolizine are obtained, which corresponds to a yield of 59%.

M.p.: 108°–111° C. (under decomposition).

EXAMPLE 7

(±)-Cis-14-ethoxycarbonyl-14-hydroxyamino-eburnane (3αH,16αEt)

A solution of 0.39 g (5.65 mmoles) of sodium nitrite in 5 ml of water is added to a solution of 0.75 g (1.885 mmoles) of (±)-1α-ethyl-1β-(2'-carboxy-2'-ethoxycarbonylethyl)-1,2,3,4,6,7,12,12bα-octahydro-indolo[2,3-a]quinolizine prepared as described in Example 6, in 15 ml of glacial acetic acid. The reaction proceeds at room temperature within one hour. The reaction mixture is rendered alkaline (pH=11) with a 30% aqueous sodium hydroxide solution under very intense ice cooling, and the separated organic substance is extracted four times with 40 ml of dichloromethane, each. The dichloromethane extracts are combined, washed with 10 ml of water, dried over anhydrous magnesium sulfate, filtered, and the filtrate is evaporated in vacuo. The 0.60 g of solid obtained as a residue are triturated with 5 ml of dichloromethane, the separated substance is filtered off, washed with 3 ml of dichloromethane, and dried.

0.52 g of (±)-cis-14-ethoxycarbonyl-14-hydroxyamino-eburnane (3αH,16αEt) are obtained, which corresponds to a yield of 72%. M.p.: 156°–158° C. (from dichloromethane).

When subjected to thin layer chromatography on a silica gel KG-G plate using a 14:3 mixture of benzene and methanol, the $R_f$ value of (±)-cis-14-ethoxycarbonyl-14-hydroxyamino-eburnane (3αH,16αEt) is higher than that of the starting (±)-1α-ethyl-1β-(2'-carboxy-2'-ethoxycarbonyl-ethyl)-1,2,3,4,6,7,12,12bα-octahydro-indolo[2,3-a]quinolizine.

The title compound did not show melting point depression in admixture with (±)-cis-14-ethoxycarbonyl-14-hydroxyamino-eburnane (3αH,16αEt) prepared as described in the Hungarian patent application No. RI-634, and was identical with the latter compound with respect to all of the physical and chemical characteristics.

IR (KBr): 3400 (NH, OH), 1700 (CO) cm$^{-1}$.

$^1$H-NMR (CDCl$_3$, δ): 8.3 (1H, NH), 4.0 (2H, q, J=7.3 cps, COOCH$_2$CH$_3$), 1.18 (3H, t, J=7.3 cps, COOCH$_2$CH$_3$) ppm.

Mass spectrum (m/e, %): 383 (M$^+$, 98), 382 (59), 366 (100), 354 (10), 338 (7.7), 310 (31), 292 (29), 278 (8.5), 267 (40), 253 (92), 237 (15), 211 (18).

EXAMPLE 8

(−)-3αS,16αS-14-Ethoxycarbonyl-14-hydroxyamino-eburnane (±)-Cis-14-ethoxycarbonyl-14-hydroxyamino-eburnane (3αH,16αEt) is resolved with dibenzoyl-D-tartaric acid to obtain the title compound. M.p.: 169°–171° C. (from dichloromethane); $[α]_D^{20}$=−56.1° (c=1.05, in dimethyl formamide).

EXAMPLE 9

(±)-Cis-14-methoxycarbonyl-14-hydroxyamino-eburnane (3αH,16αEt)

One proceeds as described in Examples 2, 6 and 7 with the difference that the 8 ml of methylenemalonic acid diethyl ester is replaced by an equivalent amount of methylenemalonic acid dimethyl ester.

The title compound melts at 179° C. (from methanol).

IR (KBr): 3420 (NH, OH), 1710 (CO$_2$CH$_3$) cm$^{-1}$.

$^1$H-NMR (CDCl$_3$, δ): 8.05 (1H, NH), 7.6–7.0 (4H, m, aromatic protons), 3.5 (3H, s, CO$_2$CH$_3$), 1.1 (3H, t, CH$_2$CH$_3$) ppm.

Mass spectrum: m/e 70 eV, M$^+$=369.

Analysis: calculated for C$_{21}$H$_{27}$N$_3$O$_3$ (mol.wt.: 369.14): C: 68.27%, H: 7.36%, N: 11.38%; found: C: 68.58%, H: 7.29%, N: 11.28%.

EXAMPLE 10

(±)-Cis-14-ethoxycarbonyl-14-hydroxyamino-eburnane (3αH,16αEt)

8.00 g of a mixture of (±)-1α-ethyl-1β-(2',2'-diethoxycarbonyl-ethyl)-1,2,3,4,6,7,12,12bα-octahydro-indolo[2,3-a]quinolizine and (±)-1α-ethyl-1β-(2',2',4',4'-tetraethoxycarbonyl-butyl)-1,2,3,4,6,7,12,12bα-octahydro-indolo-[2,3-a]quinolizine perchlorates, prepared as described in Example 2, are dissolved in 80 ml of dichloromethane. The solution is shaken with 40 ml of a 5% aqueous sodium carbonate solution, the organic phase is separated, dried over anhydrous magnesium sulfate, filtered, and the filtrate is evaporated to dryness in vacuo. The oily residue is dissolved in 80 ml of ethanol, a solution of 1.00 g of potassium hydroxide in 4 ml of water is added, and the reaction mixture is allowed to stand at room temperature for 3.5 hours.

Thereafter the solvent is evaporated in vacuo, the oily residue is dissolved in 16 ml of water, and the solution is extracted twice with 8 ml of benzene, each.

32 ml of glacial acetic acid are added to the aqueous phase, the mixture is cooled in an ice bath, and a solution of 2.00 g of sodium nitrite in 4 ml of water is added dropwise within 10 minutes. The mixture is allowed to stand at room temperature for one hour, thereafter the pH of the mixture is adjusted to 9 with a 30% aqueous sodium hydroxide solution under intense cooling with ice. The resulting mixture is extracted thrice with 50 ml of ethyl acetate, each. The organic phases are combined, washed with 20 ml of water, dried over anhydrous magnesium sulfate, filtered, and the filtrate is evaporated in vacuo, to obtain 4.00 g of a solid residue.

This solid residue is recrystallized from 20 ml of dichloromethane to obtain 3.44 g of the title compound, which is identical with that obtained according to Example 7. This corresponds to a yield of 65% calculated for the 5.00 g of the perchlorate mixture used as starting substance.

What we claim is:

1. A compound of the formula (VII)

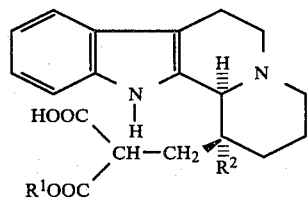

wherein $R^1$ and $R^2$ are each $C_1$ to $C_6$ alkyl, or a pharmaceutically acceptable salt thereof.

2. The compound defined in claim 1 which is (±)-1α-ethyl-1β-(2'-carboxy-2'-ethoxycarbonyl-ethyl)-1,2,3,4,6,7,12,12bα-octahydro-indolo[2,3-a]quinolizine or a pharmaceutically acceptable salt thereof.

3. A process for the preparation of a compound of the formula (I)

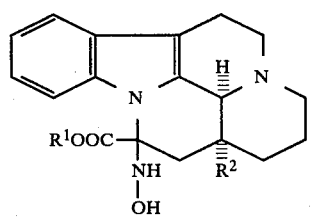

wherein $R^1$ and $R^2$ are each $C_1$ to $C_6$ alkyl or a pharmaceutically acceptable acid addition salt thereof which comprises the step of:

nitrosating a compound of the formula (VII)

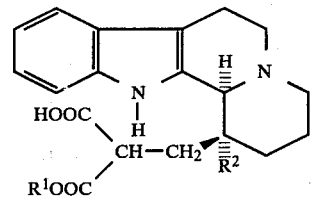

or a pharmaceutically acceptable salt thereof in the presence of an acid with a compound selected from the group consisting of an alkali nitrite and a $C_1$ to $C_6$ alkyl nitrite to yield the desired product.

4. The process defined in claim 3 wherein the compound of the formula (VII) is formed by the step of treating a reaction mixture comprising compounds of the formulae (Va) and/or (Vb) or pharmaceutically acceptable acid addition salts thereof

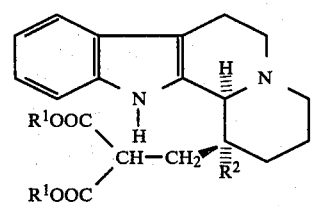

(Va)

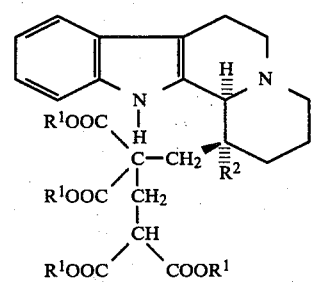

(Vb)

and an inert organic solvent with an inorganic base at a temperature between room temperature and the boiling temperature of the reaction mixture.

5. A process for the preparation of a compound of the formula (VII)

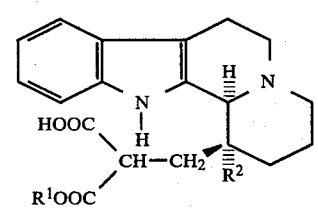

or a pharmaceutically acceptable salt thereof which comprises the step of treating a reaction mixture comprising the compounds of the formulae (Va) and/or (Vb)

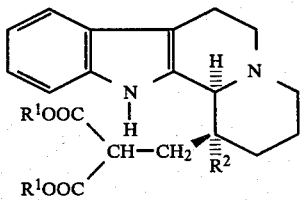

(Va)

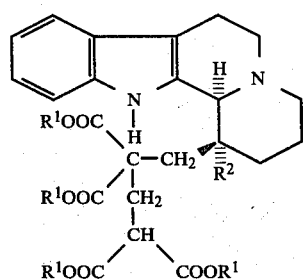

or pharmaceutically acceptable acid addition salts thereof and an inert organic solvent with an inorganic base at a temperature between room temperature and the boiling temperature of the reaction mixture to form the desired product.

6. The process defined in claim 3 wherein the nitrosating compound is an alkali nitrite and the acid is glacial acetic acid.

7. The process defined in claim 3 wherein the nitrosating compound is a $C_1$ to $C_6$ alkyl nitrite in an inert organic solvent and the acid is an alcoholic acid solution.

8. The process defined in claim 4 or claim 5 wherein the inert organic solvent is a mixture of water and an alcohol of the formula $R^1$—OH and the inorganic base is an alkali hydroxide.

* * * * *